| United States Patent [19] | [11] | 4,394,374 |
|---|---|---|
| Ushijima | [45] | Jul. 19, 1983 |

[54] THYMUS GLAND EXTRACTS

[76] Inventor: Richard N. Ushijima, 43 Nanea Ave., Wahiawa, Hi. 96786

[21] Appl. No.: 273,581

[22] Filed: Jun. 15, 1981

[51] Int. Cl.³ ............................................. A61K 7/32
[52] U.S. Cl. .................................................... 424/95
[58] Field of Search .......................................... 424/95

[56] References Cited

U.S. PATENT DOCUMENTS 3,657,417  4/1972  Brunetti et al. ...................... 424/95
4,239,498  12/1980  Rule ..................................... 424/95

OTHER PUBLICATIONS

Goldstein et al., Proc. Nat. Acad. Sci. U.S.A., vol. 56, (1966), pp. 1010–1017, and vol. 69, No. 7, (1972), pp. 1800–1803.

*Primary Examiner*—Sam Rosen
*Attorney, Agent, or Firm*—Klarquist, Sparkman, Campbell, Leigh, Whinston & Dellett

[57] ABSTRACT

A process for the manufacture of a new thymus gland extract is disclosed. Comminuted thymus glands are mixed with hot distilled water which dissolves target protein substances. After a period of time, solids and liquid fats are separated from the aqueous solution. The solution is mixed with a large volume of a sulfate salt to form a pricipitate containing a high yield of the target substances.

16 Claims, No Drawings

THYMUS GLAND EXTRACTS

SUMMARY OF THE INVENTION

The present invention relates to the solvent extraction of physiologically active substances from biological materials. More particularly, the invention relates to the extraction of chemical substances from thymus glands.

In recent years, it has been discovered that thymic hormones produce a variety of physiological effects when administered to animal subjects. Such substances are particularly useful in treating animals which are born without a properly functioning thymus gland. In addition, animal studies have shown thymic hormones may be useful in treating certain other disorders.

The thymic hormones are present in extracts obtained from thymus glands. Such extracts, which contain a variety or protein materials, are administrated in injectable solutions.

Although there are many uses and potential uses for thymic extracts, they are not widely available. This is because the known extraction techniques are costly and difficult.

Commonly, thymus extracts are obtained by combining chopped thymus glands with a NaCl solution to form a precipitate which is discarded. A large volume of an organic solvent such as acetone is added to the supernatent solution to form another precipitate. The new precipitate is extracted with saline solution, and the extract further purified. An example of such a procedure is described in Goldstein, et al., "Preparation, Assay, and Partial Purification of Thymic Lymphocytopoietic Factor (Thymosin)." *Proc. Nat. Acad. Sci. USA*, Vol. 56; pp 1010-1017 (1966).

Such procedures are cumbersome in that they include numerous steps. Yields are lower than desired, because the glands are first combined with a saline solution. This can cause premature precipitation and loss of some desired substances. Furthermore, large quantities of costly petroleum-desired organic chemicals are employed. And, after use, an environmentally acceptable technique must be used to dispose such materials.

It has now been discovered that high yields of thymus extract substances can be obtained using a new extraction technique which employs water as the only solvent. With the new procedure, chemical precipitating agents are recoverable for reuse. And, good yields of thymus extract substances are obtained at a low cost and with no detrimental impact on the environment.

The method of the present invention produces an extract effective for treating certain conditions, such as weak-calf syndrome, as in an amount and potency equal to that of extracts obtained by prior processes. However, an additional volume of extract is obtained by the present process. This additional volume is effective in treating certain particular conditions, so that the overall yield is increased. The overall extract obtained by the present process is thus of greater volume than extracts obtained by prior techniques.

An object of this invention is to provide a new thymus extract which when administered to a human or other animal subject will produce a medically useful physiological effect.

A further object is to produce a thymus extract with a minimum of procedural steps and apparatus.

Also an object is to manufacture a thymus extract in high yield and at low cost.

Still another object is to manufacture a thymus extract without the use of organic compounds which are costly and create a waste disposal problem.

These and other objects, advantages and features of this invention will be apparent from the following detailed description.

DETAILED DESCRIPTION

The present invention is a method for producing a medically useful extract of the thymus gland using distilled water as a primary solvent. In the process, edible grade thymus glands from cattle or pigs are defatted and then comminuted by grinding. Each 300 grams of ground glands are blended with between 400 and 600 ml. of distilled water. The mixture is heated at a sufficient temperature and amount of time that large proteins and proteolytic enzymes are at least partially denatured. Such conditions exist when the mixture is held in a hot water bath at between 65° C. and 90° C. for at least five minutes. Optimum results require holding at temperature for ten to fifteen minutes. Temperatures of 100° C. or greater are avoided since they can cause the break down of some desired high molecular weight substances.

The heated mixture is mechanically separated. For example, if the material is centrifuged, it will separate into three layers or fractions. The bottom layer will contain solid materials, the middle an aqueous solution, and the top a liquid fat or oil layer. The aqueous fraction is separated for further processing.

To the aqueous fraction is added an amount of sulfate salt, preferably ammonium sulfate, sodium sulfate, or mixtures thereof, to form a precipitate. Ammonium sulfate is preferred because it can easily be removed by dialysis. Seven parts of the aqueous fraction obtained after centrifuging are combined with between 9.5 and 11 parts of saturated ammonium sulfate solution. Alternatively, another sulfate ion source could be added in the amount required to obtain an equal yield of precipitate. The precipitate which results from a sulfate addition contains the desired thymic substances.

A great volume of the desired thymic substances come out of solution; and experiments indicate that the precipitate includes a different assay of substances than thymus extracts manufactured according to prior processes. Although the exact assay of the precipitate and chemical reaction path are unknown, it is believed that use of the specified high concentration of sulfate ions produces this unique precipitate.

The precipitate is separated from the supernatant liquid by centrifuging. Then the precipitate is combined with at least two, and preferably between eight and ten volumes of distilled water for a sufficient period of time that a portion of the precipitate dissolves to form an extract solution. The resulting solution and undissolved precipitate are subjected to dialysis whereby all dissolved sulfate salt and other low molecular weight substances, if any, are removed. This desalted extract solution is separated from the undissolved precipitate by centrifuging. The remaining aqueous solution contains a thymus extract having proteins and polysaccharide protein complexes.

The resulting extract is sampled to determine its protein content and then formulated in useful dosage units. For example, it can be combined with saline to form an injectable solution of a desired protein concentration. The extract may also be lyophilized for storage.

When used to treat humans or other animals subjects, the thymus extract of the present invention is found to be suitable for treatment of the same diseases and conditions which have been successfully treated by prior thymus extracts. Surprisingly, however, extracts made by the present process can be used to formulate a greater number of dosage units per gram of comminuted glands if the extract is used to treat certain conditions such as weak-calf syndrome. For some other uses, the extract has an equal or slightly greater effect than prior extracts.

Tests with animals indicate that extracts obtained using a lower sulfate dosage are effective in treating virtually all conditions which respond to thymus extract therapy. However, the additional volume of extract obtained by precipitating with a large quantity of sulfate, while of reduced effectiveness against certain conditions, is of full potency against others. Thus, by using a relatively high amount of sulfate to induce precipitation, the overall yield of thymus extract is greatly increased provided that the resulting product is used for specific conditions.

EXAMPLE 1

Frozen, edible grade thymus glands from cattle were partially thawed and defatted. The defatted glands were then passed through a meat grinder having holes of approximately 3/16 inch diameter. About 300 grams (approximately 250 ml.) of the ground glands were combined with 500 ml. of distilled water at about 90°–95° C. The mixture was blended together for one minute in a "Waring-type" blender.

The mixture was then heated for about ten minutes in a hot water bath maintained between 70° C. and 85° C. After heating, the mixture was centrifuged at between 3,000 and 4,000 rpms for ten minutes. During centrifuging, three observable layers formed.

An upper layer comprised liquid fat. This was removed by suction and discarded. A middle layer of aqueous solution was collected by decanting. The lowest layer, comprising solids, was discarded.

A precipitate was formed from the aqueous solution by combining seven parts of the solution with ten parts of a saturated ammonium sulfate solution (550 g/l) at about pH 7. The precipitate started to form within about five minutes. After cooling overnight at room temperature, the mixture of liquid and precipitate was centrifuged at between 3,000 and 4,000 rpms for about five minutes; and the precipitate was separated from the supernatent aqueous solution. The precipitate was combined with ten volumes of distilled water and stirred for about two hours during which time a portion of the precipitate dissolved to form an extract solution.

The undissolved precipitate and the extract solution were then dialyzed against distilled water through a dialysis bed of 2,000 molecular weight cutoff. Dialysis proceeded for a period of three days and was conducted at refrigeration temperature to inhibit bacterial growth. The undissolved precipitate was then removed from the extract solution by centrifuging at between 10,000 and 15,000 rpms for a period of fifteen minutes. After separation the precipitate was discarded. The remaining aqueous solution contained the desired thymus extract. Approximately 0.6 gram, dry weight, of extract was obtained from each kilogram of thymus gland processed.

After dialysis, the dialysate is an aqueous solution containing primarily the sulfate salt used as a precipitating agent. This salt may be recovered from the dialysate and reused to initiate precipitate in a new volume of aqueous solution so that there are virtually no waste materials which require special disposal techniques.

Samples of the extract were used in animal tests to determine the activity of the new extract in comparison to other known thymus extracts. In each instance, the extract obtained by the process of the present invention proved equal to or superior to the prior product. In long term tests in which dogs were injected with bovine thymus extracts, there were no adverse effects. This indicates that the extracted substances are not specific to a particular species of mammal.

EXAMPLE 2

The procedure in Example 1 was repeated using a different sulfate salt as a precipitating agent. In this instance, solid sodium sulfate ($Na_2SO_4$) was added to the aqueous solution at a ratio of 250 grams of sodium sulfate per liter of collected aqueous solution. The resultant mixture was stirred to dissolve the sodium sulfate. As in the previous example, precipitate formation started within about five minutes. After about eight hours, the precipitate was collected by centrifuging and purified according to the steps of Example 1. The same high yield of extract was obtained. And, the extract performed similarly to the extract of Example 1 in tests for physiological activity.

EXAMPLE 3

It is advantageous in some situations to obtain two separate fractions of the thymus extract, each fraction having a different activity. The two fractions can be obtained by following the procedure of Example 1, but by combining seven parts of the solution with seven parts of a saturated ammonium sulfate solution. The resulting precipitate is separated from the supernatent solution by centrifuging, and then purified by the process of Example 1 and yields about 0.2 grams of extract per kilogram of glands.

An additional three parts of the saturated ammonium sulfate solution is added to the supernatent solution to form a second precipitate. The second precipitate is also purified by the process of Example 1 and yields about 0.4 grams of extract per kilogram of glands.

While I have shown and described the preferred embodiments of my invention, it will be apparent to those skilled in the art that changes may be made without departing from my invention in its broader aspects. I therefore intend the appended claims to cover all such changes and modifications as follow in the true spirit and scope of my invention.

I claim:

1. A process for producing a thymus extract in the substantial absence of added acids and organic solvents comprising:

comminuting defatted thymus glands;

mixing the comminuted glands with water at a ratio of not more than 300 g of comminuted glands per 400 ml of water;

maintaining the resulting mixture at an elevated temperature and for a time sufficient that large proteins and proteolytic enyzymes are at least partially denatured;

mechanically separating the mixture, by centrifugation or equivalent means, into oils, undissolved solids, and an aqueous solution including protein substances;

decanting to isolate the aqueous solution;

after the aforesaid steps, forming a precipitate including the protein substances by adding a source of sulfate ions to the aqueous solution in an amount sufficient to produce a precipitate yield at least as great as a yield obtained when from 400 to 600 ml. of distilled water are mixed with each 300 g. of comminuted glands to produce the aqueous solution and from 9.5 to eleven parts to saturated ammonium sulfate solution are combined with each seven parts of the aqueous solution at room temperature;

separating the precipitate from supernatant liquid by centrifugation or equivalent means;

combining the precipitate with water so that a portion of the precipitate dissolves to form an extract solution;

dialyzing the extract solution to remove dissolved, low molecular weight substances from the extract solution; and purifying the extract solution by removing any undissolved precipitate from the extract solution by centrifugation or equivalent means.

2. The process of claim 1 wherein between about eight and ten volumes of water are combined with each volume of precipitate.

3. The process of claim 1 wherein the low molecular weight substances are recycled by mixing with a new volume of the aqueous solution to form additional amounts of the precipitate including the protein substances.

4. The process of claim 1 wherein:
about 500 ml. of water is mixed with each 300 grams of comminuted glands; and
the precipitate is formed by adding about ten parts of saturated ammonium sulfate solution to each seven parts of the aqueous solution.

5. The process of claim 1 wherein:
from 400 to 600 ml. of water is mixed with each 300 grams of comminuted glands; and
the precipitate is formed by adding from 240 to 280 grams of sodium sulfate to each liter of the aqueous solution.

6. The process of claim 5 wherein:
about 500 ml. of water is mixed with each 300 grams of comminuted glands; and
between about 240 and 250 grams of sodium sulfate is added to each liter of the aqueous solution.

7. The process of claim 1 wherein the temperature is maintained at less than 100° C.

8. The process of claim 7 wherein the temperature is maintained between 65° C. and 90° C.

9. A thymus extract manufactured according to the process of claim 1.

10. The process of claim 8 wherein the precipitate is formed by adding $Na_2SO_4$ in an amount sufficient to produce a solution containing from 1.75 to 1.98 moles per liter of $Na_2SO_4$.

11. The process of claim 1 further comprising forming a second precipitate by adding an additional amount of a sulfate salt to the separated supernatent liquid.

12. The process of claim 1 wherein, to form the precipitate, at least 9.5 parts of saturated, aqueous ammonium sulfate solution are added per each seven parts of the aqueous solution that includes the protein substances.

13. The process of claim 1 wherein, to form the precipitate, at least 250 grams of solid sodium sulfate are added per liter of the aqueous solution that includes the protein substances.

14. A process for producing a thymus extract in the substantial absence of added acids and organic solvents comprising:

comminuted defatted thymus glands;

mixing from 400 to 600 ml. of a an aqueous solvent with each 300 grams of comminuted glands;

maintaining the resulting mixture at an elevated temperature sufficiently to at least partially denature large protein fractions and proteolytic enzymes;

mechanically separating the mixture, by centrifugation or equivalent means, into oils, undissolved solids, and a solution including protein substances;

decanting to isolate the the solution, after the aforesaid steps forming a precipitate including the protein substances by adding a source of sulfate ions to the solution in an amount sufficient to produce a precipitate yield at least as great as a yield obtained when from 9.5 to 11 parts of saturated ammonium sulfate solution are combined with seven parts of the solvent solution at room temperature;

separating the precipitate from supernatent liquid by centrifugation or equivalent means;

combining the precipitate with water so that a portion of the precipitate dissolves to form an extract solution;

dialyzing the extract solution to remove dissolved, low molecular weight substances from the extract solution; and purifying the extract solution by removing any undissolved precipitate from the extract solution by centrifugation or equivalent means.

15. The process of claim 14 wherein:
the defatted thymus glands are comminuted by grinding to a pulp;
the aqueous solvent is hot water;
the maintaining at an elevated temperature is accomplished in a hot water bath from 65° C. to 90° C. for ten to fifteen minutes;
the mechanically separating is accomplished by centrifuging;
the oils are removed by suction;
the solution including protein substances is separated from the undissolved solids by pouring off the liquid;
the sulfate salt is selected from the group consisting of $(NH_4)_2SO_4$, $Na_2SO_4$, and mixtures thereof;
the precipitate is separated from supernatent liquid by centrifugation; and
the precipitate is combined with about ten volumes of water for a sufficient time that a portion of the precipitate is dissolved to form an extract solution.

16. A process for producing two distinct thymus extracts in the substantial absence of added acids and organic solvents comprising:

comminuted defatted thymus glands;

mixing the comminuted glands with water at a ratio of not more than 300 g of comminuted glands per 400 ml of water;

maintaining the resulting mixture at an elevated temperature and for a time sufficient that large proteins and proteolytic enyzymes are at least partially denatured;

mechanically separating the mixture, by centrifugation or equivalent means, into oils, undissolved solids, and an aqueous solution including protein substances;

decanting to isolate the aqueous solution;

after the aforesaid steps, forming a first precipitate including protein substances by adding source of sulfate ions to the aqueous solution in an amount sufficient to produce a precipitate yield not greater than a yield obtained when from 400 to 600 ml of distilled water are mixed with each 300 grams of comminuted glands to produce the aqueous solution and seven parts of saturated ammonium sulfate solution are combined with each seven parts of the aqueous solution at room temperature;

separating the first precipitate from supernatant liquid by centrifugation or equivalent means;

forming a second precipitate including protein substances by adding a source of sulfate ions to the supernatant liquid;

separately purifying each of the precipitates by combining each precipitate with water so that portions of the precipitates are dissolved to form extract solutions;

separately dialyzing the extract solutions to remove dissolved, low molecular weight substances from the extract solutions; and separately purifying the extract solutions by removing any undissolved precipitates from the extract solutions.

* * * * *